(12) United States Patent
Shan et al.

(10) Patent No.: US 9,770,212 B2
(45) Date of Patent: Sep. 26, 2017

(54) DEVICE AND METHOD FOR EXTRACTING PHYSIOLOGICAL INFORMATION

(71) Applicant: KONINKLIJKE PHILIPS N.V., Eindhoven (NL)

(72) Inventors: Caifeng Shan, Eindhoven (NL); Ihor Olehovych Kirenko, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 14/417,564

(22) PCT Filed: Jul. 26, 2013

(86) PCT No.: PCT/IB2013/056141
§ 371 (c)(1),
(2) Date: Jan. 27, 2015

(87) PCT Pub. No.: WO2014/020509
PCT Pub. Date: Feb. 6, 2014

(65) Prior Publication Data
US 2015/0208987 A1    Jul. 30, 2015

Related U.S. Application Data

(60) Provisional application No. 61/678,653, filed on Aug. 2, 2012.

(51) Int. Cl.
*A61B 5/00* (2006.01)
*A61B 5/08* (2006.01)
(Continued)

(52) U.S. Cl.
CPC .......... *A61B 5/7278* (2013.01); *A61B 5/0077* (2013.01); *A61B 5/024* (2013.01);
(Continued)

(58) Field of Classification Search
CPC ......... A61B 5/05; A61B 5/113; A61B 5/7285; A61B 5/7289; A61B 5/0816; A61B 5/4818; G06K 9/2027
See application file for complete search history.

(56) References Cited

U.S. PATENT DOCUMENTS 8,542,877 B2     9/2013  Jeanne et al.
8,634,591 B2 *   1/2014  Jeanne ............... G06K 9/00496
                                                        382/103
(Continued)

FOREIGN PATENT DOCUMENTS

WO    2010/100593      9/2010
WO    2010100594 A2    9/2010
(Continued)

*Primary Examiner* — Joel Lamprecht (57) ABSTRACT

Physiological information is extracted from detected electromagnetic radiation emitted or reflected by a subject (10). A data stream (30) derivable from the electromagnetic radiation is received. The data stream (30) includes a sequence (76; 152) of signal samples (78a, 78b, 78c; 154a, 154b, 154c) indicative of desired subject motion and of disturbing motion, the signal samples representing at least one region of interest (84; 164) and at least one non-indicative motion region (86; 166). The at least one defined region of interest (84; 164) exhibiting an at least partially periodic indicative motion pattern attributable to at least one physiological parameter (56), and a disturbing motion portion. A sequence (158) of motion compensated samples (80; 160a, 160b, 160c) at least partially compensated for undesired overall motion is derived. At least one characteristic signal (90; 112) at least partially indicative of the at least partially periodic indicative motion pattern is derived from the sequence (158) of derived motion compensated samples (80; 160a, 160b, 160c).

19 Claims, 6 Drawing Sheets

(51) Int. Cl.
*A61B 5/11* (2006.01)
*A61B 5/113* (2006.01)
*G06T 7/254* (2017.01)
*A61B 5/024* (2006.01)

(52) U.S. Cl.
CPC .............. *A61B 5/0816* (2013.01); *A61B 5/11* (2013.01); *A61B 5/113* (2013.01); *A61B 5/1128* (2013.01); *A61B 5/7207* (2013.01); *G06T 7/254* (2017.01); *A61B 5/02416* (2013.01); *G06T 2207/10016* (2013.01); *G06T 2207/30004* (2013.01)

(56) References Cited

U.S. PATENT DOCUMENTS

| | | |
|---|---|---|
| 8,649,562 B2 | 2/2014 | De Haan et al. |
| 8,805,019 B2 | 8/2014 | Jeanne et al. |
| 2010/0061596 A1 | 3/2010 | Mostafavi et al. |
| 2010/0130873 A1* | 5/2010 | Yuen ................ A61B 5/0205 600/484 |
| 2012/0116202 A1 | 5/2012 | Bangera et al. |
| 2014/0037166 A1 | 2/2014 | De Haan et al. |
| 2014/0088433 A1 | 3/2014 | Shan |

FOREIGN PATENT DOCUMENTS

| | | |
|---|---|---|
| WO | 2011/042839 | 4/2011 |
| WO | 2011042858 A1 | 4/2011 |
| WO | 2013/027027 | 2/2013 |

* cited by examiner

ID MEDIA AND METHOD FOR EXTRACTING PHYSIOLOGICAL INFORMATION

CROSS REFERENCE TO RELATED APPLICATIONS

This application is a national filing of PCT application Serial No. PCT/IB2013/056141, filed Jul. 26, 2013, published as WO 2014/020509 A1 on Feb. 6, 2014, which claims the benefit of U.S. provisional application Ser. No. 61/678,653 filed Aug. 2, 2012, which is incorporated herein by reference.

FIELD OF THE INVENTION

The present invention relates to a device and a method for extracting physiological information from detected electromagnetic radiation emitted or reflected by a subject, wherein the physiological information is embedded in a data stream comprising a sequence of signal samples indicative of desired subject motion and of disturbing motion.

BACKGROUND OF THE INVENTION

U.S. 2010/0061596 A1 discloses a method of determining a similarity with a portion of a physiological motion, the method comprising the steps of:
  obtaining a first image of an object;
  obtaining a second image of the object;
  determining a level of similarity between the first and second image; and
  correlating the determined level of similarity between first and second images with a portion of the physiological motion.

The document further discloses several refinements of the method. In particular, the document is directed to patient monitoring, such as monitoring breathing activity of a patient. Vital signal monitoring grows in significance in several fields of application, such as patient monitoring and monitoring sports and fitness activities. Further beneficial applications can be envisaged. Although considerable progress in the field of monitoring performance has been achieved, it is still a challenge to provide for instant signal recognition and signal processing enabling immediate, so-to-say, on-line detection of desired vital signals. This applies in particular to hand-held mobile devices commonly lacking of sufficient computing power.

A further challenge may arise from disturbances and further constraints which have to be taken into account for the detection of the desired signals. As known in the art, detection quality can be improved through applying obtrusive (or: tactile) measurement. For monitoring breathing activity or, in other words, respiration activity, obtrusive measurement devices may comprise belts or sensors which typically have to be attached to a subject's body. Furthermore, referring to remote detection approaches, prior art devices and methods may require markers or similar items which have to be applied to the subject to be observed. These markers can be remotely monitored since they provide sufficient "detectability" and may be considered a prominent target for a detecting device. Still, however, obtrusive measurement, either applied remotely or via tactile measurement devices, is considered unpleasant and uncomfortable by many observed subjects.

Remote unobtrusive measurement typically aims at recording or monitoring the subject of interest without applying any components or "hardware" to the subject at all.

Consequently, since no hardware markers are available, remote unobtrusive detection is widely subjected to disturbances. Recently, even mobile hand-held devices for remote monitoring of vital signals have been envisaged. Mobile hand-held devices are even more susceptible to disturbances since they are commonly hand-operated without fixed support.

Therefore, it has to be expected that the recorded data, such as captured reflected or emitted electromagnetic radiation (e.g., recorded image frames) comprises major signal components deriving from overall disturbances. Disturbance-related signal components overlay and affect the desired vital signals basically addressed when monitoring the subject. Overall disturbances may be attributed to changing luminance conditions and disturbing motion components. Disturbing motion may arise from non-indicative motion of the subject itself, or from undesired motion of the detecting or sensing device. In particular with mobile hand-held monitoring devices, overall motion (or: global motion) is considered a huge challenge. Furthermore, particularly addressing respiration detection via remote unobtrusive measurement devices, subject motion-related signals are, so-to-say, attenuated in case the subject of interest is covered, for instance by clothes or even blankets. This applies in particular when sleeping or lying subjects are addressed. Under such conditions, even removal of a blanket would be considered an unpleasant obtrusive measure.

After all, vital signal detection becomes even more difficult when amplitudes and/or nominal values of disturbing signal components are expected to be much larger than amplitudes and/or nominal values of desired signal components to be extracted. Potentially, the magnitude of difference between the respective components (e.g., global motion vs. respiration motion) can be expected to even comprise several orders.

A possible approach to this challenge may be directed to providing well-prepared and steady ambient conditions when capturing a signal of interest in which the desired vital signal component is embedded. A minimization of potentially occurring disturbing signal components can be achieved in this way. However, such "laboratory" conditions cannot be transferred to everyday field applications and environments, since high efforts and preparation work would be necessary therefore.

The required preparation work might comprise, by way of example, installation and orientation of several defined standard light sources and, moreover, measures for fixation of the subject to be observed so as to avoid disturbing motion. It is considered unlikely that these measures are applicable in everyday environments, for instance, ambulant or clinical patient monitoring, or even in lifestyle environments like sporting and fitness monitoring.

SUMMARY OF THE INVENTION

It is an object of the present invention to provide a device and a method for extracting physiological information from detected electromagnetic radiation providing further refinements facilitating obtaining the desired vital signals with reduced efforts. It would be further advantageous to provide a device and a method adapted for being less susceptible to disturbances, in particular to disturbances arising from global motion. Furthermore, it would be advantageous to provide for signal detection approaches well-suited for mobile devices and applications typically suffering from severe motion influences.

In a first aspect a device for extracting physiological information from detected electromagnetic radiation emitted or reflected by a subject is presented, the device comprising:

an interface for receiving a data stream derivable from electromagnetic radiation emitted or reflected by a subject, the data stream comprising a sequence of signal samples indicative of desired subject motion and of disturbing motion, the signal samples representing at least one region of interest and at least one non-indicative motion region, the at least one defined region of interest exhibiting an at least partially periodic indicative motion pattern attributable to at least one physiological parameter, and a disturbing motion portion; and a processing unit configured for processing the sequence of signal samples, comprising:

a stabilizing means configured for deriving a sequence of derivative motion compensated samples at least partially compensated for undesired overall motion;

an extractor means configured for deriving at least one characteristic signal at least partially indicative of the at least partially periodic indicative motion pattern from the sequence of derivative motion compensated samples; and a signal enhancement means configured for processing the at least one characteristic signal under consideration of overall motion residue occurring in the derivative motion compensated samples, thereby generating at least one enhanced characteristic signal.

The present invention is based on the insight that, when addressing remote signal detection, often huge motion-related disturbances non-indicative of the signals of interest are present in the detected data. In other words, the presence of huge distortions has to be "accepted" and dealt with. Moreover, basically the same holds true for data which already has undergone motion compensation measures. The device of the invention is particularly suited for remote signal detection applications indented for operation without obtrusive markers or similar items.

In the field of remote vital signal detection, motion compensation is often addressed. For instance, a transitional shift between two or more consecutive samples (or: image frames) can be estimated through adequate image processing algorithms. Shift information can be utilized for compensating the samples for undesired motion so as to "stabilize" the sequence. However, in this connection, it should be noted that the sequence of signal samples indeed comprises a considerably minute motion pattern of interest primarily addressed. Therefore, "smoothening" the sequence of image samples by directly transferring commonly known image processing algorithms may level the signals and, consequently, remove the desired signal components. However, since characteristics of the desired subject motion can be predicted (e.g., in terms of expected frequency bands and amplitudes), adequate filtering or similar processing measures can be considered suitable approaches to this issue.

Up to this point, motion compensation can contribute in enhancing a signal-to-noise ratio. Still, however, a certain amount of signal components related to undesired overall motion are still expected to be present in the "motion compensated" signal samples. In other words, since motion compensating algorithms are adapted for allowing indicative motion patterns to "pass", also disturbance-related motion components may somewhat "leak" the sequence of derivative motion compensated samples. Such motion residue can render the detection and extraction of the desired vital signals even more cumbersome.

The present invention addresses this issue by providing for a device which is configured to taking into account the motion residue. Basically, this can be achieved by processing the at least one region of interest and the at least one non-indicative motion region on a comparative basis. Consequently, the device of the invention can make use of the fact that the region of interest is considered to be both indicative of desired motion and, to some extent, indicative of undesired motion or, more precisely, undesired motion residue. On the other hand, the at least one non-indicative motion region is considered to primarily comprise motion residue-affected signals. Therefore, comparative processing may attenuate or even remove motion residue information overlaying both the region of interest and the non indicative motion region.

The device of the invention is particularly suited for, but not limited to, detecting a subject's respiration rate, respiration rate variability, or related derivative parameters. Occurrence and expectable characteristics of such vital signals can be readily predicted or assumed to a certain extend. In other words, by way of example, when aiming at an extraction of the subject's present breath rate, it can be assumed that a cycle of breathing in and breathing out is represented by a characteristic repetitive lifting and lowering of the chest portion and/or the abdominal portion of the subject's body. Needless to say, respiration can also be represented by characteristic motion of a face portion of the subject (e.g., nasal wings or mouth portions). Basically, indicative subject motion can be considered physiological information since it is representative of the underlying desired vital signals. In general, the term indicative motion pattern may refer to indicative subject motion-related characteristics (such as frequency and/or amplitude) sought in the sequence of signal samples. As used herein, the term sequence may refer to a continuous or discrete series of signal samples.

The data stream may comprise a sequence of frames or, more precisely a series of image frames. For instance, RGB-images comprising color information can be utilized. However, also frames representing infrared (IR) and red (R) information can form the sequence of frames. The image frames can represent at least a portion of the observed subject and further elements.

There exist several embodiments of the stabilizing means, the extractor means and the signal enhancement means. In a first, fairly simple embodiment, the stabilizing means, the extractor means and the signal enhancement means are commonly embodied by the processing unit which is driven (or: controlled) by respective logic commands (or: program code). Such a processing unit may also comprise suitable input and output interfaces and, furthermore, additional processing means.

However, in the alternative, each or at least some of stabilizing means, the extractor means and (if any) further processing means can be embodied by separate processing units which are controlled or controllable by respective logic commands. Hence, each respective processing means can be adapted to its special purpose. Consequently, a distribution of tasks can be applied, where distinct tasks are processed (or: executed) on distinct single processors of a multi-processor processing unit, or wherein image processing related tasks are executed on an image processor, while other operational tasks are executed on a central processing unit.

According to an advantageous embodiment the processing unit further comprises an analyzing means configured for determining temporal variations in the enhanced characteristic signal, the temporal variations being representative of at least one vital signal. Basically, the enhanced characteristic signal can be considered highly indicative or representative of the at least one physiological parameter and, at least in a mediate way, of the desired vital signal, in particular of the subject's respiration rate, respiration rate variability, or of respective derivates. Preferably, the desired vital signal is clearly detectable in the at least one enhanced characteristic signal. Signal processing methods can be utilized for extracting the desired signal.

According to yet another embodiment the extractor means is further configured for deriving the characteristic signal from the region of interest, and for deriving a disturbance-related signal from the non-indicative motion region. Signal derivation can be applied on the sequence level. That is, slight changes within the motion of interest can be tracked or detected over time so as to achieve the respective derived signals. As indicated above, the characteristic signal may comprise both the desired indicative motion information and, moreover, disturbance-related motion (residue) information. The disturbance-related signal, on the other hand, is basically considered to primarily comprise disturbance-related motion information since no indicative motion subject motion is expected in the non-indicative motion region.

According to another embodiment the extractor means is further configured for deriving the disturbance-related signal from at least one defined motion-related non-indicative region of interest selected in the non-indicative motion region. By way of example, the motion-related non-indicative region of interest can be considered a subset of the non-indicative motion region. It is preferred that the motion-related non-indicative region of interest and the (indicative) region of interest are spaced from one another in a signal sample. In other words, a neighboring region adjacent to the (indicative) region of interest may still be slightly indicative of the desired signals since the region of interest is typically chosen so as to clearly exhibit the desired signals. Therefore, the region of interest may be composed of a subset of a region potentially indication for the subject's indicative motion.

This embodiment is based on the idea that a supplementary reference region may be chosen as a proper basis for the derivation of the disturbance-related signal. Typically, remote vital signal detection includes selection of a region of interest which is considered to be highly indicative of the desired signals. However, as indicated above, also the region of interest is at least partially distorted by motion (residue) information. This applies even for embodiments in which the sequences of signal samples undergo motion compensation algorithms. It is therefore considered beneficial to explicitly select a defined region in the signal samples which assumingly is not representative of the desired signals. Consequently, through comparative processing the characteristic signal and the disturbance-related signal, a signal "offset" can be detected. Based on this "offset" the enhanced characteristic signal can be generated.

It is further desirable that the extractor means is configured for individually applying an extraction algorithm to the region of interest, and to the non-indicative motion region. Also the extraction algorithm can be directed to the sequence (or: series) level of the signal subsets. In other words, both the region of interest and the non-indicative motion region can be separately processed according to the same or basically the same algorithm. In particular, the extraction algorithm can be directed to detect the desired indicative motion patterns which are considered highly representative of the desired signals. Since the subject's motion may basically comprise slight periodic lifting and lowering (or: forth and back motion) at a certain frequency in an assumed frequency band, with respect to a surrounding non-indicative region (e.g., a background in an image frame), the desired motion typically involves a defined orientation (or: direction).

In one embodiment the extraction algorithm further involves directly or indirectly detecting edges which are attributed to the subject's motion. It should be further noted that a single (or: common) algorithm may be applied separately to both the region of interest and the non-indicative motion region. Needless to say, the non-indicative motion region is considered to be not indicative of the desired vital signals at all. Still, however, applying the extraction algorithm may finally lead to some result, namely the disturbance-related signal. Even though the disturbance-related signal is basically heavily distorted, a comparative processing approach can make use of it since the underlying disturbing motion portion may basically also be present in the region of interest. Consequently, the disturbance-related signal can be utilized for further compensating the characteristic signal for undesired motion residue.

In yet another embodiment the signal enhancement means is further configured for generating the enhanced characteristic signal under consideration of the disturbance-related signal. A motion residue-compensated enhanced characteristic signal can be derived in this way.

According to yet another aspect the signal enhancement means is further configured for deducting the disturbance-related signal from the characteristic signal. Hence, the "signal offset" can be deducted. Since motion residue information is therefore further attenuated or removed, the signal-to-noise ratio can be further improved in this way.

According to yet another embodiment the device further comprises a sensor means configured for capturing electromagnetic radiation within at least one particular wavelength range selected from the group consisting of visible light, infrared light, and ultraviolet radiation, the sensor means being connectable to the interface. As used herein, the term sensor means may also refer to a sensor means comprising a plurality of sensors. For instance, the sensor means may comprise an array of CCD-sensors. The array of sensors may be formed as a line array or as a two-dimensional array. As mentioned above, the indicative motion pattern typically involves a dominant motion orientation or direction. In other words, desired subject motion often can be referred to as basically one-dimensional motion. Therefore, given that a suitable orientation between the sensor means and the subject of interest is achieved, also a sensor means making use of a line array of sensors can be utilized for signal detection measures. Nevertheless, also a sensor means comprising a two-dimensional array of sensors can be used for signal detection measures.

In particular, commonly known RGB-cameras can be used for monitoring the subject of interest. By contrast, in particular when poor illumination conditions have to be expected also infrared cameras can be envisaged. A sensor means capable of capturing infrared radiation may be suitably adapted for monitoring hardly illuminated subjects. This applies in particular when visible light is barely present in the monitoring environment. By way of example, this may apply to overnight monitoring of patients. According to yet another embodiment the device further comprises at least one source of illumination configured for emitting radiation. Basically, the device can be configured for capturing and processing electromagnetic radiation deriving directly or indirectly from ambient illumination. Still, however, providing distinct illumination sources may improve the quality and detectability of the underlying signals since in this way disturbances related to changing illumination conditions can be reduced.

It should be noted in this connection that, in a preferred embodiment, the device may be configured as a mobile device, in particular a hand-held portable device comprising a housing accommodating the sensor means. Such a mobile device may also comprise the at least one source of illumination. The mobile device may be further provided with the processing unit. Moreover, the device, in particular in a mobile device configuration, may further comprise a display for presenting information. The display may be implemented as a screen. However, alternatively or in addition, the device may also comprise visual indicators, haptic indicators, acoustic indicators and such like indicators. It is further worth mentioning that the device can be implemented in a mobile phone or tablet computing environment.

According to yet another embodiment the at least one source of illumination is further configured for visually indicating at least one of the region of interest and the motion-related non-indicative region of interest. As used herein, the term "visually indicating" may refer to highlighting or "visually" marking the respective regions. This can be achieved by directing high-contrast visible light of a certain shape (e.g., having a defined light beam or cone) to at least a certain portion of the subject of interest and of the surrounding region. The emitted radiation can be shaped and configured such that a user of the device readily becomes aware of the region of interest and the motion-related non-indicative region of interest.

According to yet another aspect the device further comprises a sensor means configured for detecting electromagnetic radiation, wherein at least one of the at least one source of illumination and the sensor means are matched such that at least one of the region of interest and the motion-related non-indicative region of interest can be visually indicated by the at least one of the at least one source of illumination and captured by the sensor means.

In other words, a field of view of the sensor means and an emitting angle or light beam of the at least one source of illumination can be adapted to each other. Matching the sensor means and the at least one of the at least one source of illumination can be performed on a fixed basis. So, when in operation, the device may highlight certain predefined regions, depending on an actual orientation. This embodiment comprises several features which are similar to hand-held bar code scanners or similar devices. In this way, the device can even make profit from the fact that hand-held devices typically have no set or fixed orientation. A user holding the device can direct the sensor means and the at least one source of illumination such that the highlighted portions cover respective indicative portions, namely a portion of the subject representing the chest or abdominal region thereof, and a non-indicative distinct (reference) region.

According to yet another embodiment the analyzing means is further configured for applying an integral transformation, in particular a Fourier transformation, to the at least one enhanced characteristic signal, thereby obtaining frequency information attributable to the desired indicative subject motion pattern representative of the vital signal. In this way, a sequence of magnitude ranges indicative of the desired vital signals can be obtained. Consequently, a dominant frequency in the enhanced characteristic signal can be representative of the desired vital signal, for instance the respiration rate.

In a further aspect of the present invention, a method for extracting physiological information from detected electromagnetic radiation emitted or reflected by a subject is presented, the method comprising the steps of:

receiving a data stream derivable from electromagnetic radiation emitted or reflected by a subject, the data stream comprising a sequence of signal samples indicative of desired subject motion and of disturbing motion, the signal samples representing at least one region of interest and at least one non-indicative motion region, the at least one defined region of interest exhibiting an at least partially periodic indicative motion pattern attributable to at least one physiological parameter, and a disturbing motion portion; and processing the sequence of signal samples, comprising:
    deriving a sequence of derivative motion compensated samples at least partially compensated for undesired overall motion;
    deriving at least one characteristic signal at least partially indicative of the at least partially periodic indicative motion pattern from the sequence of derivative motion compensated samples; and
    processing the at least one characteristic signal under consideration of overall motion residue occurring in the derivative motion compensated samples, thereby generating at least one enhanced characteristic signal.

Advantageously, the method can be carried out utilizing the device for extracting physiological information of the invention.

According to an embodiment the method further comprises the steps of:
    deriving the characteristic signal from the region of interest; and
    deriving a disturbance-related signal from the non-indicative motion region, in particular from at least one defined motion-related non-indicative region of interest.

In yet another aspect of the present invention there is provided a computer program which comprises program code means for causing a computer to perform the steps of the processing method when said computer program is carried out on a computer.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing system which may involve or make use of computing capacity provided in a cloud environment.

Preferred embodiments of the invention are defined in the dependent claims. It shall be understood that the claimed methods and the claimed computer program can have similar preferred embodiments as the claimed device and as defined in dependent device claims.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figures 1, 2:
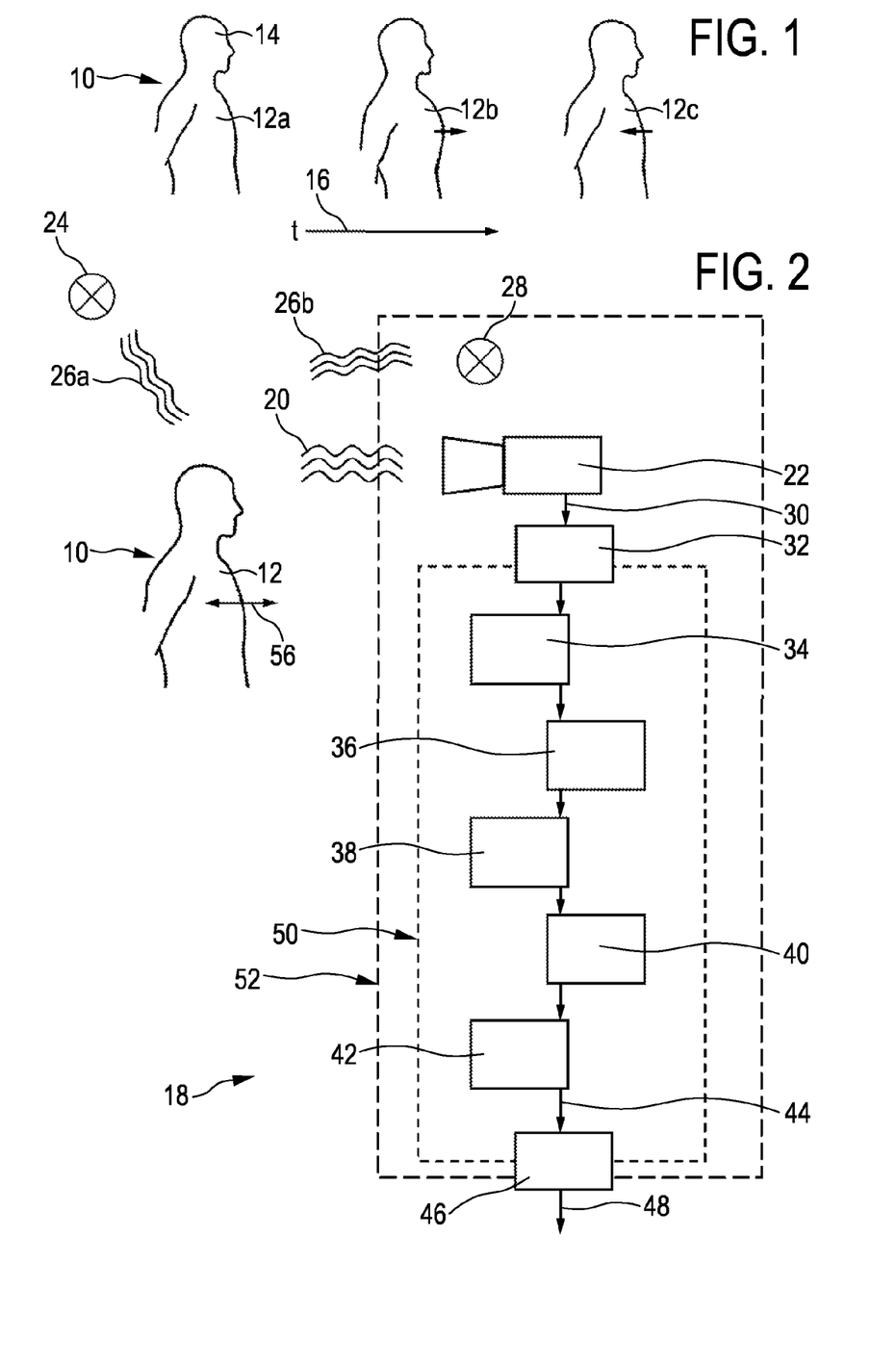
FIG. 1 shows a schematic illustration of subject motion indicative of an exemplary vital signal.
FIG. 2 shows a schematic illustration of a general layout of a device in which the present invention can be used.

FIG. 1 shows a schematic illustration of a subject 10 which experiences motion indicative of a signal of interest. The subject 10 undergoes a characteristic motion of an indicative portion 12 due to respiration. When breathing, expansion and contraction of the lungs or the diaphragm causes slight motion of characteristic portions of living beings, in particular lifting and lowering of the chest. Also abdominal breathing can cause characteristic motion of respective parts of the subject's body. At least partially periodic motion patterns induced by various physiological processes can occur in many living beings, particularly in humans or animals. Over time, as indicated by an arrow 16, the indicative portion 12 is moved between a contracted position, indicated by reference numerals 12a, 12c, and an extracted position, indicated by reference numeral 12b. By way of example, based on this motion pattern (herein also referred to as physiological information 56, refer to FIG. 2) the respiration rate or respiration rate variability can be assessed. While the indicative portion 12 is pulsating over time, a non-indicative portion 14 remains substantially motionless (in terms of the desired motion pattern). Certainly, also the non-indicative portion 14 can undergo diverse motion over time. However, this motion does not correspond to the periodic pulsation of the indicative portion 12.

Now referring to FIG. 2, a device for extracting information is illustrated and denoted by a reference numeral 18. The device 18 is particularly suited for detecting motion of an indicative portion 12 of the subject 10 related to physiological information, refer also to the arrow 56 in this regard. The device 18 can be utilized for recording image frames representing the subject 10. The image frames can be derived from electromagnetic radiation 20 emitted or reflected by the subject 10. For extracting information from the recorded data, e.g. from a sequence of image frames, a defined part or portion of the subject 10 can be observed by a sensor means 22. The sensor means 22 can be embodied, by way of example, by a camera adapted to capture information belonging to at least one spectral component of the electromagnetic radiation 20. The sensor means 22 may comprise an array of single sensor elements. For instance, the sensor means 22 can make use of a line array or of a matrix array of single sensors, such as charge-coupled devices (CCD-sensors). Still, however, also alternative sensor types can be utilized. It is worth noting that the device 18 also can be configured for processing input signals, namely an input data stream, already recorded in advance and, in the meantime, stored or buffered. In this connection, recording can be performed by separate remote sensor means.

As indicated above, the electromagnetic radiation 20 can contain a continuous or discrete characteristic signal which is considered to be highly indicative of the at least one partially periodic vital signal but, on the other hand, typically massively distorted by overall disturbances such as global motion and varying illumination conditions. In some embodiments, the device can make use of defined illumination sources or, in general, radiation sources 24, 28. Illumination source 24 can be considered an ambient separate source of radiation. Illumination source 28 can be considered an internal controllable source of radiation. The radiation sources 24, 28 basically emit incident radiation 26a, 26b striking the subject 10. Typically, the incident radiation 26a, 26b is at least partially reflected by the subject 10. Furthermore, for embodiments making use of infrared or deep-infrared radiation, also the subject 10 may emit (or: generate) radiation portions, such as thermal radiation.

Known methods for obtaining vital signals such as respiration-related signals comprise tactile respiration rate monitoring and remote respiration rate monitoring relying on markers applied to the subject of interest. To this end, however, obtrusive monitoring is required. As indicated above, an alternative approach is directed to remote unobtrusive measuring utilizing specific image processing methods.

The sensor means 22 can be configured for delivering a data stream 30 to an interface 32. Needless to say, also a buffer means could be interposed between the sensor means 22 and the interface 30. Downstream of the interface 32 a stabilizing means 34 may be provided. Basically, the stabilizing means 34 can be configured for applying motion compensation measures to the data stream 30. This way, a sequence of signal samples embedded in the data stream 30 can be transformed into a sequence of derivative motion compensated samples. At this level, motion compensation is directed to overall motion which can be caused by relative movement between the subject 10 and the sensor means 22. A monitoring environment typically comprises at least a part of the subject 10, peripheral elements such as walls, furniture or even non-indicative portions of the subject 10 and the sensor means 22. Among these elements undesired relative motion can occur. In particular for mobile applications making use of hand-held portable devices 18 or, at least, sensor means 22, the detected sequence of signal samples can be heavily affected by shaking or blurring effects caused on the end of the sensor means 22. Typically, these undesired disturbances exceed the desired motion patterns in magnitude. As indicated above, primary motion compensation measures may result in signal samples which may still contain motion-related disturbances, hereinafter referred to as motion residue. The present invention basically tackles this issue.

The sequence of motion compensated signal samples can be delivered to an extractor means 36. The extractor means 36 can be configured for deriving at least one characteristic signal from the sequence of derivative motion compensate samples. For instance, the extractor means 36 can be adapted for seeking minute slight periodic motion in the sequence which can be attributed to the desired vital signal of interest.

Still, the characteristic signal derived in this way is considered to be distorted by the afore-mentioned motion residue which is still present after primary motion compensation measures. Therefore, in a preferred embodiment, the extractor means can be further configured for deriving a disturbance-related signal which is assumingly distorted by motion residue as well but, however, not indicative of the desired motion pattern. Basically, the characteristic signal derivation can be directed to a defined region of interest representing at least a part of the indicative portion 12 in the subject 10. By contrast, the disturbance-related signal derivation can be directed to a distinct region of interest chosen within a non-indicative motion region in the signal samples. The non-indicative motion region may contain a representation of set background or surrounding elements present in the monitoring environment. Typically, these elements are expected to be stationary or immobile. Therefore, at least a portion of the non-indicative motion region can be utilized as a reference region of interest allowing for comparative analysis eventually resulting in an enhanced characteristic signal having a considerably high signal-to-noise ratio.

Also a signal enhancement means 38 can be provided in the device 18. The signal enhancement means 38 can be configured for processing the at least one characteristic signal under consideration of overall motion residue occurring in the derivative motion compensated samples. An enhanced characteristic signal can be generated by the signal enhancement means 38. Generating the enhanced characteristic signal may be based on the characteristic signal derived from the region of interest and can, preferably, involve consideration of the disturbance-related signal. In one embodiment, the disturbance-related signal can be deducted from the characteristic signal. In this way, a motion residue-related "offset" can be removed from the characteristic signal.

The device 18 may further comprise an analyzing means 40 configured for determining temporal variations of the enhanced characteristic signal. In particular, the analyzing means 40 can be adapted for seeking for dominant frequencies attributable to the desired vital signals of interest. Hence, the analyzing means 40 can make use of several signal processing approaches. For instance, the analyzing means 40 can be configured for applying a Fourier transformation or a similar integral transformation to the enhanced characteristic signal so as to obtain frequency values or even a frequency domain representation of the enhanced characteristic signal.

Furthermore, a (post-)processing means 42 can be provided which can be configured for even further enhanced signal quality. To this end, the processing means 42 can be adapted for applying filtering functions, clipping functions, windowing functions, weighting functions, statistical evaluations and such like. Eventually, a processed data stream 44 can be generated by the processing unit 50. The processed data stream 44 can be delivered to an interface 46. Consequently, via the interface 46 output data 48 can be made available for further analysis and/or for display measures. The (input) interface 32 and the (output) interface 46 can be embodied by the same (hardware) interface elements. The stabilizing means 34, the extractor means 36, the signal enhancement means 38, and (if any) the analyzing means 40 and the processing means 42 can be jointly embodied by a common processing unit 50. Also the interfaces 32, 46 can be connected thereto in a common processing device accommodating the respective subcomponents. By way of example, the processing unit 50 can be embodied by a personal computer or a mobile computing device.

In case also the sensor means 22 is jointly connected to the processing unit 50 a common housing may accommodate the respective components. In this connection, an overall system boundary is indicated by a reference numeral 52. Reference numeral 52 may also refer to a common housing for the device 18. If such an integrated approach is intended, the device can be embodied by a mobile device such as a smart phone, a tablet computing device or a mobile health monitoring device. These devices can make use of an integrated sensor means (camera) 22 or at least being connectable to a separate sensor means (camera) 22. In another exemplary configuration, the device 18 is a stationary device while at least the sensor means 22 is portable. The sensor means 22 can be coupled to a stationary processing unit 50 via suitable cable connections or wireless connections.

Figure 3:
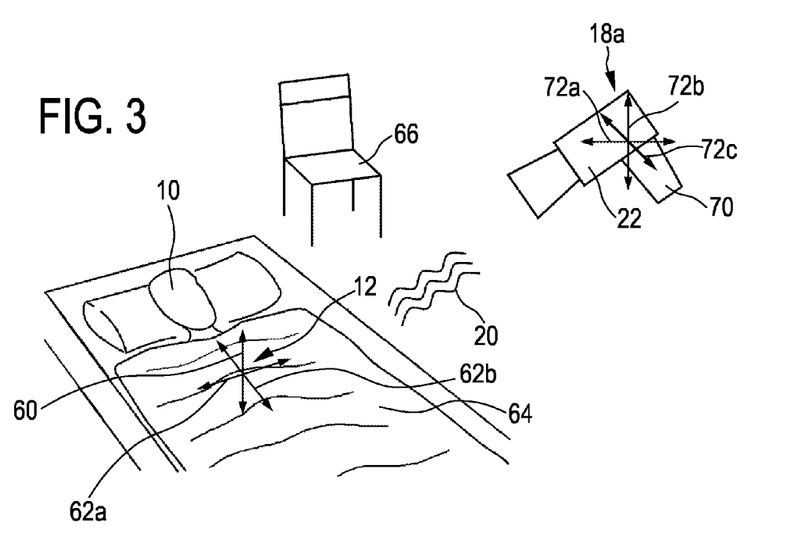
FIG. 3 shows a schematic illustration of an arrangement including a subject to be monitored.

With reference to FIG. 3, a common environment in which unobtrusive vital signal monitoring is performed is presented. The subject 10, e.g. a patient staying in bed, is resting on a support. The subject's 10 head attributable to the non-indicative portion 14 (FIG. 1) is exposed and pillowed while the indicative portion 12 (e.g., the chest) is covered by a blanket 64. Thus, the desired signal caused by motion of the indicative portion 12 is attenuated or hidden. Therefore, unobtrusive signal detection is considerably difficult. This applies in particular, when a portable mobile monitoring device 18a is utilized. The monitoring device 18a can comprise a handle 70 a user may grab for holding and orientating the device 18a. The device 18a, in particular the sensor means 22, can be positioned and orientated such that the indicative portion 12 undergoing the indicative motion pattern can be observed. In FIG. 3, an axis 60 indicates an expected direction of the periodic motion of interest. Periodic subject motion along this axis 60 can represent the desired physiological information 56. By contrast, potential subject motion in other directions, refer to reference numerals 62a, 62b, is considered to be not indicative and therefore not of a particular interest. The monitoring environment shown in FIG. 3 may further comprise stationary objects, refer to reference numeral 66. Stationary objects may serve as reference objects for motion residue compensation. Therefore, also the stationary object 66 (e.g., a chair) may be present in the field of view of the sensor means 22. For mobile or portable applications, the sensor means 22 may undergo positional changes and orientation changes when observing the subject 10. Sensor means 22 motion may comprise motion along and around several axes, refer to reference numerals 72a, 72b, 72c.

Figures 4, 5:
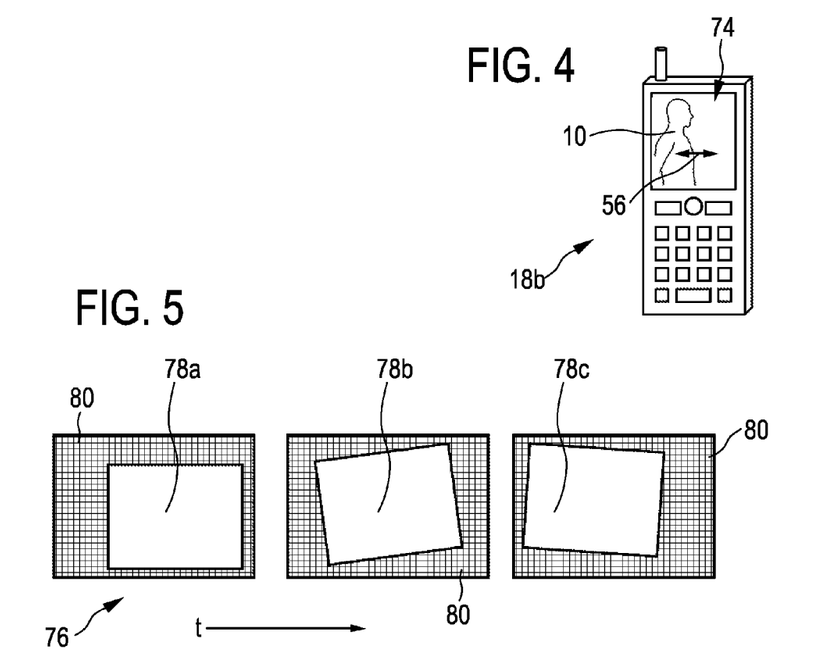
FIG. 4 shows an exemplary simplified illustration of a mobile device in which the present invention can be used.
FIG. 5 shows a simplified exemplary sequence of signal samples which are subjected to overall motion.

FIG. 4 illustrates an alternative embodiment including a mobile device 18b. Since mobile devices such as mobile phones, tablet computers and notebooks are readily available and, moreover, often include adequate cameras, suitable control algorithms can be implemented so as to control these devices in vital signal monitoring applications. The device 18b may comprise a display 74 for representing an indicative portion 12 of the subject exhibiting the desired motion pattern which is attributed to the physiological information 56. A user may therefore target the subject 10 under consideration of a present representation of the subject 10 in the display 74. Consequently, instant signal detection on a remote basis can be simplified.

FIG. 5 illustrates a sequence 76 of signal samples 78a, 78b, 78c. For illustrative purposes, also a spatial reference 80 is indicated. The sequence 76 may comprise a series of the signal samples 78a, 78b, 78c. Since motion related disturbances have to be expected, typically a field of view covered by each of the signal samples 78a, 78b, 78c may vary over the series of samples. Since these deviations are considered to exceed the desired indicative motion pattern in terms of absolute values and amplitudes, motion compensation is crucial for further processing and signal extraction. As already set out above, a sequence of motion compensated signal samples 82 (refer to FIG. 6 and FIG. 7) can be derived from the (original) sequence 76. Still, the derived sequence is considered to be adversely affected by motion residue.

Figure 6:
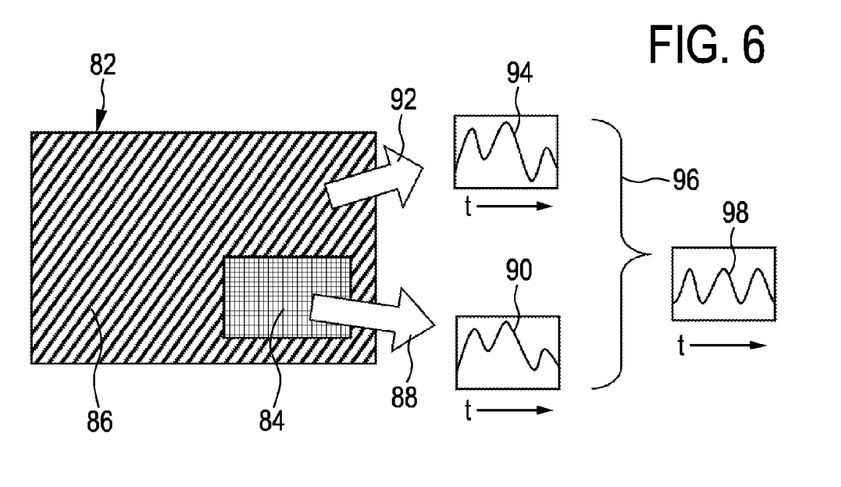
FIG. 6 illustrates an exemplary derivation approach for generating an enhanced characteristic signal.
Figure 7:
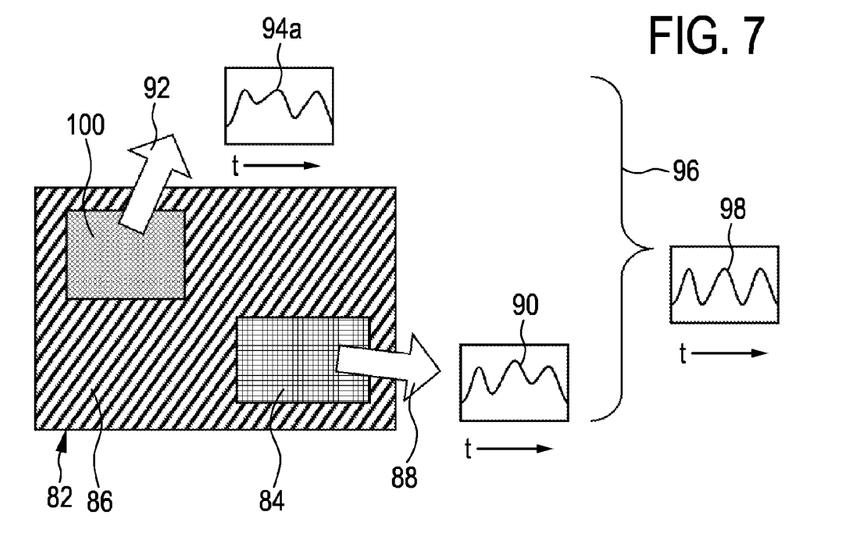
FIG. 7 shows an alternative exemplary derivation approach for generating an enhanced characteristic signal.

FIG. 6 and FIG. 7 illustrate alternative approaches for addressing these issues. Both FIG. 6 and FIG. 7 illustrate a motion compensated signal sample 82 taken from a sequence of motion-compensated signal samples derived from the (original) sequence 76. A region of interest 84 may be selected in the motion compensated signal sample 82. Basically, the region of interest 84 can be selected on a manual or an automatic basis. Non-automatic selection may comprise a manual selection of the region of interest by a user. Automatic detection may comprise image segmentation, in particular feature detection and feature tracking adapted for seeking indicative portions 12 of the subject 10 in the sequence of motion compensated signal samples 82. Based on the region of interest a characteristic signal 90 can be computed, extracted and plotted over time, refer to reference numeral 88. Still, the characteristic signal 90 is considered to contain huge motion residue-related portions. Therefore, as a reference, a disturbance related signal 94 is extracted from the (series of) motion compensated signal samples 82, refer to reference numeral 92.

To this end, basically the remaining portion of the signal sample 82 (except for the region of interest 84) can be utilized. The remaining portion (or: difference portion) may be referred to as disturbing motion portion 86. The disturbing motion portion 86 may serve as a basis for the derivation of the disturbance related signal 94. As mentioned above, both the disturbance related signal 94 and the characteristic signal 90 may contain basically the same or at least similar motion residue information. Insofar, the disturbance related signal 94 can be exploited as a reference for further processing. As indicated by a curly bracket (reference numeral 96) the characteristic signal 90 can be processed under consideration of the disturbance related signal 94 so as to generate an enhanced characteristic signal 98. For instance, the disturbance related signal 94 can be "deducted" from the characteristic signal 90. Consequently motion residue influences can be attenuated or even removed. Based on the enhanced characteristic signal 98 the desired vital signal of interest can be calculated.

FIG. 7 illustrates a similar approach. In FIG. 7, a defined non-indicative region of interest 100 is selected in the disturbing motion portion 86. Based on the non-indicative region of interest 100 a disturbance related signal 94a can be calculated. Eventually, the characteristic signal 90 can be transferred under consideration of the disturbance related signal 94a into an enhanced characteristic signal 98. A defined selection of the non-indicative region of interest 100 can be considered beneficial since in this way a certainly stationary region (e.g., furniture and the like) can be chosen within the motion compensated signal sample 82. Basically, the motion compensated signal sample 82 may represent moving or movable components. For instance, given that the region of interest 84 does not exactly "cover" the indicative portion 12 of the subject 10, even potentially indicative motion patterns may be present in the disturbing motion portion 86. Furthermore, additional motion related components may be present. This may apply to subject motion as well, for instance when the observed patient is turning in bed. Moreover, additional persons may be present in the motion compensated signal sample 82 exhibiting motion patterns which are not related to "overall" or "global" motion. Such adversely effected portions can be considered a barely appropriate basis for further processing measures. It is therefore considered beneficial to allow for a selection of the non-indicative region of interest 100 in a plain static portion of the motion compensated signal sample 82. Consequently the signal-to-noise ratio in the resulting enhanced characteristic signal 98 can be even further improved.

Figure 8:
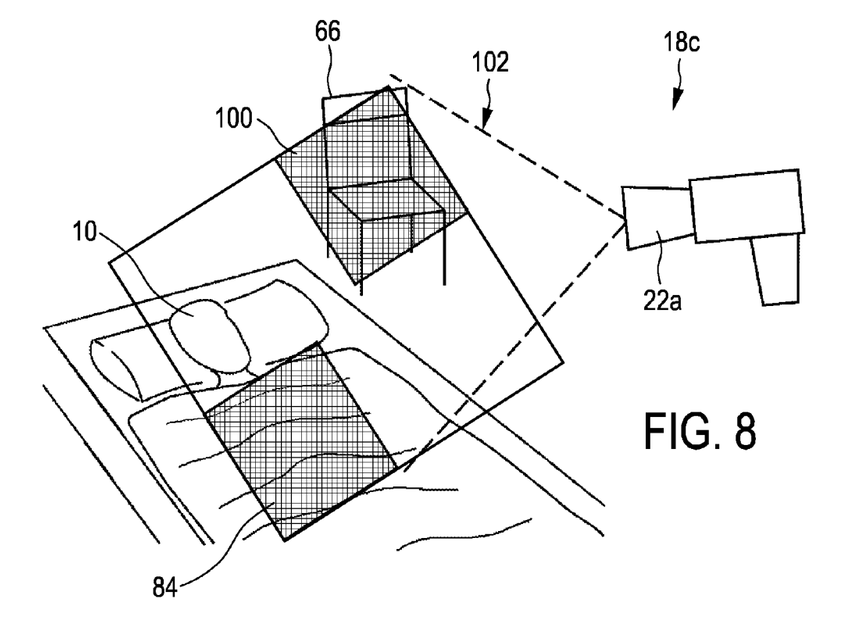
FIG. 8 shows an alternative schematic illustration of a monitoring arrangement.
Figure 9:
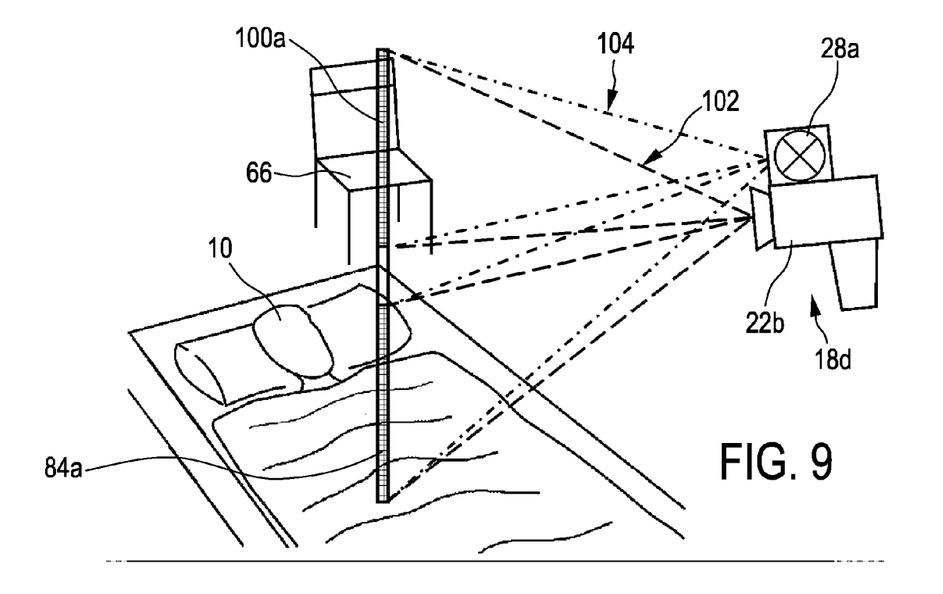
FIG. 9 shows yet another alternative schematic illustration of a monitoring arrangement.

FIG. 8 and FIG. 9 illustrate alternative monitoring environments which basically can make use of the approaches elucidated in connection with FIG. 6 and FIG. 7. In FIG. 8, a device 18c comprising a hand-held mobile sensor means 22a can be utilized. Advantageously, the region of interest 84 clearly reflects the indicative portion 12 of the subject 10. As a reference, the non-indicative region of interest 100 clearly reflects a static reference element 66 (e.g., a chair or, in general, furniture). The region of interest 84 and the non-indicative region of interest 100 are separated from each other. Therefore, mixing of indicative portions and non-indicative portions can be avoided. As indicated by a dashed line 102, the sensor means 22a may have a certain field of view. Basically, given that the sensor means 22a is configured for capturing two-dimensional frames, the field of view 102 exemplarily can be considered a rectangular section of a pyramid. Within the specific field of view 102 both the region of interest 84 and the non-indicative region of interest 100 can be selected. In one embodiment a more or less predefined arrangement of the respective regions 84, 100 can be envisaged. According to this approach a user may "target" the subject 10 and the reference element 66 by orientating the sensor means 22 (having a predefined partitioned field of view 102 which is partitioned into predefined patterns forming the region of interest 84 and the non-indicative region of interest 100)) such that the patterns for these regions 84, 100 respectively cover and capture the indicative portion 12 and the reference element 66 at the same time. A similar approach is elucidated in the following in connection with FIG. 9.

In FIG. 9 a mobile hand-held device 18d is utilized comprising a sensor means 22b and an integrated source of illumination 28a. By way of example, the sensor means 22b can be configured as a sensor means 22b having a line array of sensor elements. Since the desired motion pattern (refer to the reference numeral 56 in FIG. 2) basically involves a periodic one-dimensional motion, also a suitably orientated one-dimensional arrangement of sensor elements in the sensor means 22b can be applied. Consequently, basically a line-shaped region of interest 84a and, accordingly, a line-shaped non-indicative region of interest 100a can be selected. In one embodiment, the integrated illumination source 28a illuminates an emitting area 104 which basically matches or corresponds to the respective regions 84a, 100a (observed by the sensor means 22b). In the sensor means 22b, the regions 84a, 100a can be predefined or preselected. In this connection it is further preferred that the illumination source 28a emits visible light such that the intended regions 84a, 100a can be clearly marked. Given the exemplary embodiment in FIG. 9, the device 18d can be configured such that a straight illumination line is clearly visible to the user. The illumination line may comprise two separate portions representing the region of interest 84a and the non-indicative region 100a. Comparable arrangements are basically known in the field of logistics, warehouse management and the retail shop sector. In these fields, bar code readers or bar code scanners are commonly applied. Still, however, the device 18d provides for two distinct or separate regions 84a, 100a. Bringing the device 18d in a correct orientation and position, the indicative portion 12 of the subject 10 and the static reference element 66 can be observed. It goes without saying that the predefined regions 84a, 100a may also be formed as two-dimensional patterns.

Figure 10:
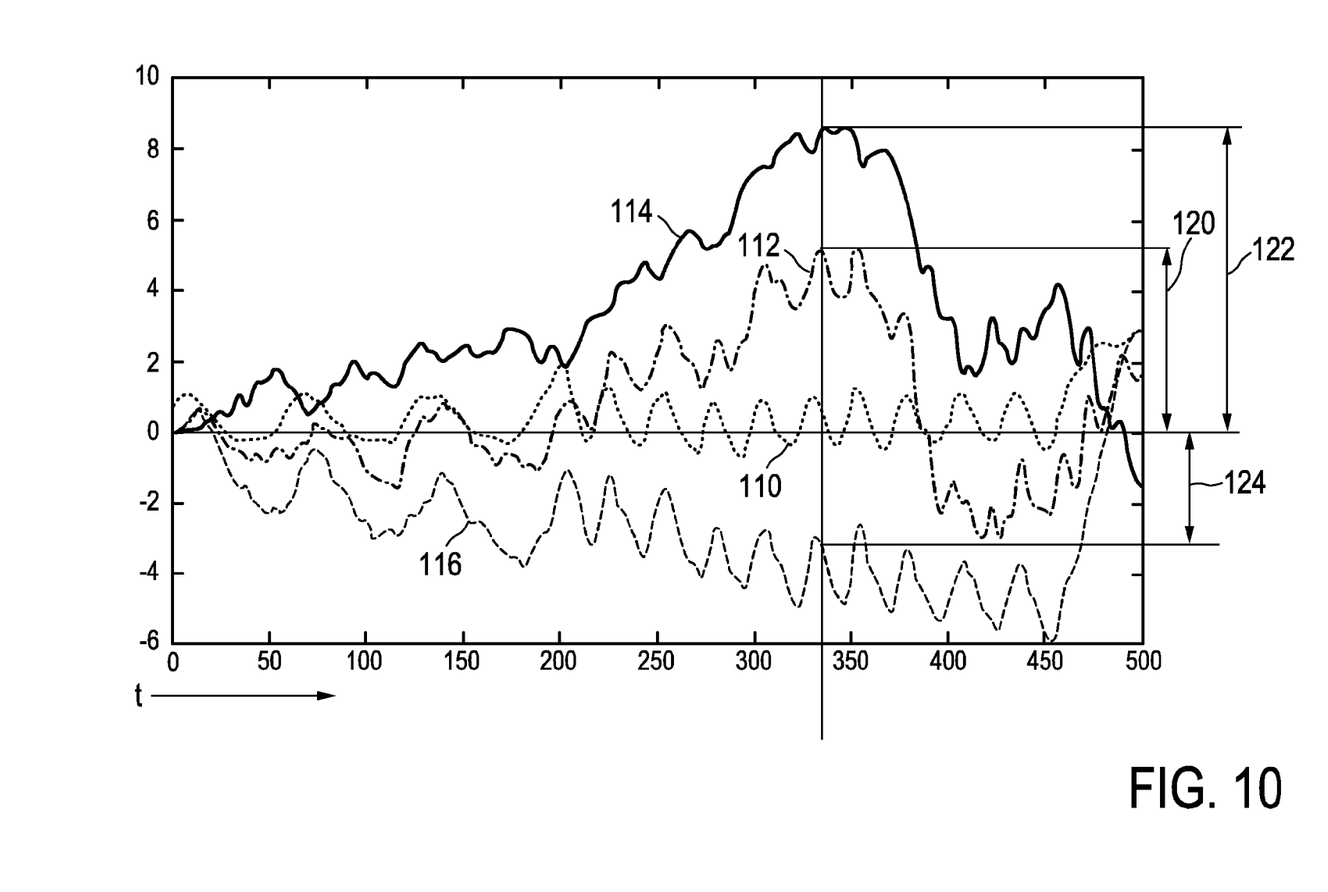
FIG. 10 exemplifies several signals related to desired subject motion and to non-indicative motion residue.

FIG. 10 illustrates several exemplary signal forms 110, 112, 114, 116 obtained through vital signal monitoring directed to the detection of a subject's 10 respiration rate (or: breath rate). An axis of abscissas denotes time (or, as in FIG. 10, frame number) while an ordinate axis may denote quantitative or qualitative signal parameters. Each of the displayed signal forms 110, 112, 116 is derived from motion-related signals attributable to motion of the indicative portion 12 of the subject 10, either directly or in a mediate way. Signal form 110 illustrates a reference signal basically obtained through obtrusive measurement. Signal form 114 illustrates a disturbance-related signal and may correspond to the disturbance-related signal 94 obtained from the non-indicative region of interest 100. Signal form 112 basically stands for a characteristic signal which may correspond to the characteristic signal 90 obtained from the region of interest 84. Signal form 114 can be deducted from signal form 112 so as to compensate for motion residue still present in both signal forms 112, 114. Consequently, a signal form 116 representing an enhanced characteristic signal and basically corresponding to the enhanced characteristic signal 98 can be generated. In this connection, for illustrative purposes, reference numerals 120, 122, 124 are referred to. Considering the zero-line, it is readily understood that deducting a certain value 122 of the signal form 114 from a respective value 120 of the signal form 112 may result in a value 124 (here: "negative" value) forming part of the enhanced signal form 116. Compared to the reference signal form 110, the signal form 116 representing the enhanced characteristic signal may still comprise disturbances. However, exemplarily referring to respiration rate determination, periodic changes are clearly visible and can therefore be processed and analyzed so as to derive at the desired vital signal of interest.

Figure 11:
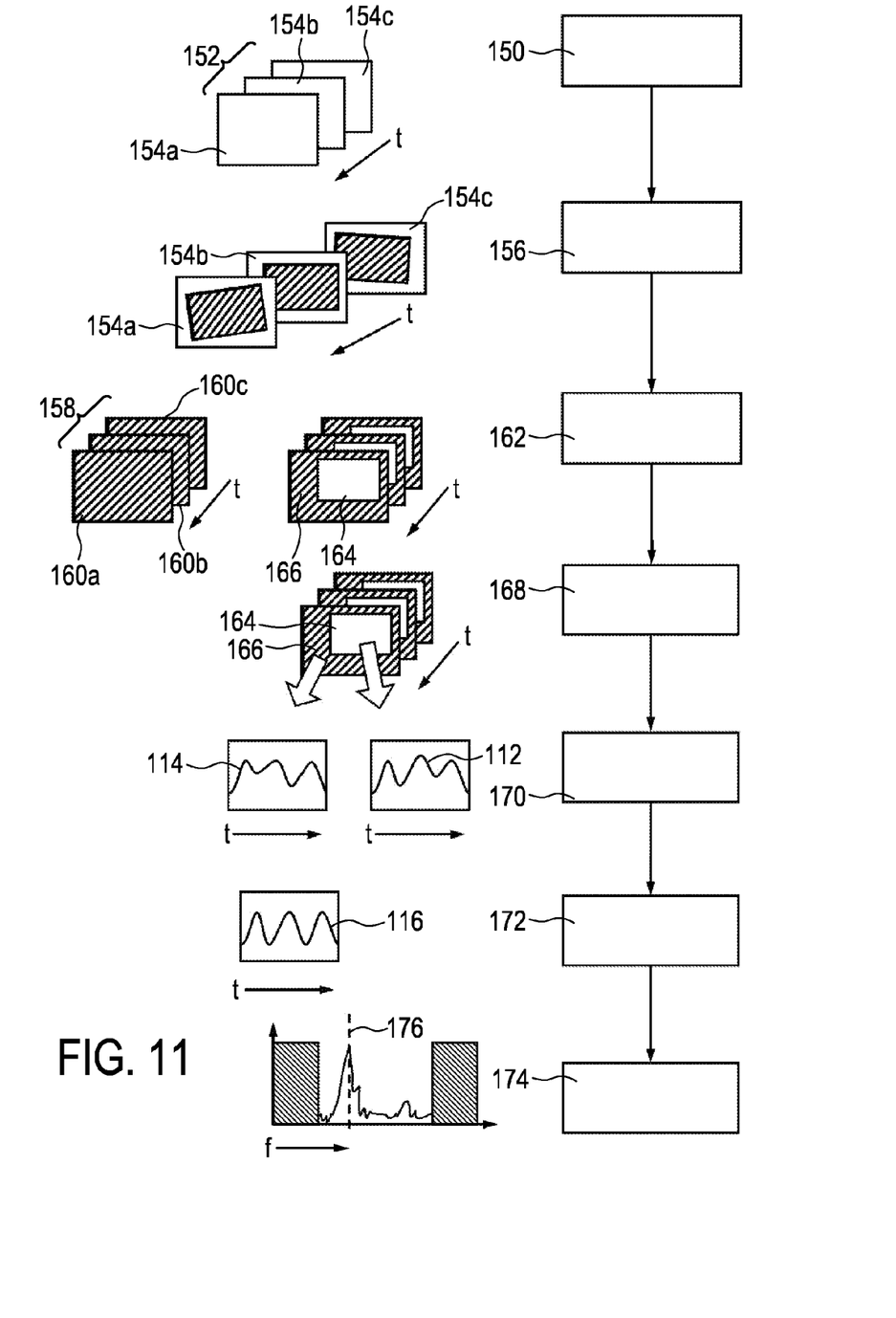
FIG. 11 shows an illustrative block diagram representing several steps of an embodiment of a method according to the invention.

Having demonstrated several alternative exemplary approaches covered by the invention, FIG. 11 is referred to, schematically illustrating a method for extracting information from detected electromagnetic radiation. Initially, in a step 150 an input data stream comprising a sequence 152 of signal samples 154a, 154b, 154c is received. An arrow t denotes time or actual frame number. The data stream can be delivered from a sensor means 22 or a data buffer or storage means. The data stream can be embodied by a series of image frames varying over time.

In a subsequent step 156 motion compensation measures can be applied to the samples 154a, 154b, 154c so as to arrive at a sequence 158 of motion compensated samples 160a, 160b, 160c. Global motion or overall motion can be induced by sensor motion, or camera motion, in particular with hand-held mobile device applications.

In a further step 162 a region of interest 164 highly indicative of the desired signals can be selected in the samples. Upon selection of the region of interest 164 also a disturbing motion portion 166 can be determined. In an alternative embodiment, furthermore, a non-indicative region of interest (refer to reference numeral 100 in FIG. 7) can be selected.

A signal extraction step 168 may follow. Signal extraction may involve a derivation of a characteristic signal 112 from the region of interest 164. Furthermore, a disturbance-related signal 114 can be derived from the disturbing motion portion 166. As already indicated above, the derivation of the disturbance-related signal 114 can also be performed under consideration of a defined non-indicative region of interest within the disturbing motion portion 166.

In a subsequent step 170 motion residue compensation can be applied. Motion residue compensation can involve processing the characteristic signal 112 under consideration of the disturbance-related signal 114. By way of example, the disturbance-related signal 114 can be deduced from the characteristic signal 112. Through motion residue compensation 170 eventually an enhanced characteristic signal 116 can be generated.

Moreover, post-processing measures can be applied to the signals in a subsequent step 172. Post-processing may comprise filtering, windowing, clipping, weighting and further adequate processing algorithms. Consequently, a signal-to-noise ratio can be further improved so as to further facilitate detection of the vital signal of interest 176.

In yet another step 174 signal analysis measures can be applied to the enhanced characteristic signal 116 so as to seek for particular characteristics indicative of at least one desired vital signal 176. Signal analysis 174 may comprise transforming the enhanced characteristic signal 116 which is based in the time domain into a transformed signal which is based in the frequency domain.

Needless to say, in an embodiment of a method in accordance with the invention several of the steps provided can be carried out in changed order, or even concurrently. Further, some of the steps could be skipped as well without departing from the scope of the invention. This applies in particular to several alternative signal processing steps.

By way of example, the present invention can be applied in the field of health care, e.g., unobtrusive remote patient monitoring, general surveillances, security monitoring and so-called lifestyle environments, such as fitness equipment, or the like. Applications may involve monitoring of respiration rate, respiration rate variability and related vital signals.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for extracting physiological information from detected electromagnetic radiation emitted or reflected by a subject, comprising:
   an interface configured for receiving a data stream derivable from electromagnetic radiation emitted or reflected by a subject, the data stream comprising a sequence of signal samples indicative of periodic physiological motion and non-periodic physiological motion, the signal samples representing at least one region of interest and at least one non-periodic motion region, the at least one defined region of interest exhibiting periodic indicative motion pattern attributable to at least one physiological parameter, and non-periodic physiological motion portion; and a processing unit configured for processing the sequence of signal samples, comprising:
a stabilizing means configured for deriving a sequence of derived motion compensated samples compensated for overall motion;
an extractor means configured for deriving at least one characteristic signal indicative of the periodic indicative motion pattern from the sequence of derived motion compensated samples, wherein the extractor means is further configured for deriving the characteristic signal from the region of interest, for deriving a non-periodic motion-related signal from the non-periodic motion region, and for individually applying an extraction algorithm to the characteristic signal from the region of interest, and to the non-periodic motion-related signal from the non-periodic motion region; and
a signal enhancement means configured for processing the at least one characteristic signal under consideration of overall motion residue occurring in the derived motion compensated samples, thereby generating at least one enhanced characteristic signal.

2. The device as claimed in claim 1, wherein the processing unit further comprises an analyzing means configured for determining temporal variations in the enhanced characteristic signal, the temporal variations being representative of at least one vital signal.

3. The device as claimed in claim 1, wherein the extractor means is further configured for deriving the non-periodic motion-related signal from at least one defined motion-related non-indicative region of interest selected in the non-indicative motion region.

4. The device as claimed in claim 3, wherein the signal enhancement means is further configured for generating the enhanced characteristic signal under consideration of the non-periodic motion-related signal.

5. The device as claimed in claim 4, wherein the signal enhancement means is further configured for deducting the non-periodic motion-related signal from the characteristic signal.

6. The device as claimed in claim 1, further comprising a sensor means configured for capturing electromagnetic radiation within at least one particular wavelength range selected from the group consisting of visible light, infrared light, and ultraviolet radiation, the sensor means being connectable to the interface.

7. The device as claimed in claim 1, further comprising at least one source of illumination configured for emitting radiation.

8. The device as claimed in claim 7, wherein at least one of the at least one source of illumination is further configured for visually indicating at least one of the region of interest and the non-periodic motion region.

9. The device as claimed in claim 7, further comprising a sensor means configured for detecting electromagnetic radiation, wherein at least one of the at least one source of illumination and the sensor means are matched such that at least one of the region of interest and the non-periodic motion region can be visually indicated by the at least one of the at least one source of illumination and captured by the sensor means.

10. The device as claimed in claim 2, wherein the analyzing means is further configured for applying a Fourier transformation to the at least one enhanced characteristic signal, thereby obtaining frequency information attributable to the periodic physiological motion representative of the vital signal.

11. A method for extracting physiological information from detected electromagnetic radiation emitted or reflected by a subject, comprising:
receiving a data stream derivable from electromagnetic radiation emitted or reflected by a region of interest and by a periodic physiological motion non-indicative reference region of interest of a subject, the data stream comprising a sequence of frames indicative of (1) periodic physiological motion and of disturbing body motion and changes in illumination from the region of interest and (2) the disturbing body motion and the changes in illumination from the reference region; and
processing the sequence of frames, comprising:
compensating the series of frames for overall global motion,
deriving a region of interest characteristic signal from the region of interest of the frames,
deriving a reference signal from the periodic physiological motion non-indicative reference region,
deducting the reference signal from the region of interest characteristic signal to generate a periodic physiological motion characteristic signal, and
transforming the periodic physiological motion characteristic signal to obtain frequency values indicative of the periodic physiological motion.

12. A non-transitory computer readable medium carrying program code configured to control a computer to carry out the steps of the method as claimed in claim 11.

13. A handheld device for extracting physiological information from electromagnetic radiation emitted or reflected by a subject, the device comprising:
a sensor configured to detect the electromagnetic radiation and convert the detected radiation into a data stream including a sequence of frames;
one or more processors configured to:
compensate the series of frames for movement between the sensor and the subject,
extract region of interest signals from a region of interest of the subject, the region of interest signals being indicative of periodic physiological motion and non-periodic body motion,
extract reference region signals from the series of frames, the reference region signals being indicative of the non-periodic body motion,
deducting the reference signals from the region of interest signals to generate characteristic signals,
post-processing the characteristic signals, the post-processing including at least one of filtering, windowing, clipping, and weighting,
transforming the post-processed characteristic signals from a time domain into a frequency domain, the transformed characteristic signal being indicative of a periodicity of the periodic physiological motion;
a display device controlled by the one or more processors to generate a display indicative of the periodicity of the periodic physiological motion.

14. The portable device as claimed in claim 13, further including a light source configured to illuminate at least the region of interest of the subject.

15. The portable device as claimed in claim 13, wherein the sensor includes a one or two-dimensional video camera.

16. The portable device as claimed in claim 13, wherein the transforming includes Fourier transforming the post-processed characteristic signal.

17. The portable device as claimed in claim 13, further including a handle configured for a user to manually hold the portable device.

18. The portable device as claimed in claim 13, wherein the portable device is incorporated into a mobile phone.

19. The portable device as claimed in claim 13, wherein the region of interest signal and the reference signals are both indicative of variations in lighting.

* * * * *